United States Patent [19]

McRae

[11] Patent Number: Plant 6,660

[45] Date of Patent: Mar. 7, 1989

[54] HYBRID ASIATIC LILY NAMED RUBY PIXIE

[75] Inventor: Edward A. McRae, Boring, Oreg.

[73] Assignee: Melridge, Inc., Aurora, Oreg.

[21] Appl. No.: 80,498

[22] Filed: Jul. 31, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant of very short stature, about 35 to 45 cm. in height, bearing clusters of flowers of medium size particularly characterized by their vivid red coloration, broad tepals, and inconspicuous spotting, the flowers being of upright orientation and the plant having abundant foliage comprising moderately long and full leaves. The short stature of this plant, its abundant foliage and its upright flower orientation make it especially suitable as a pot plant variety and its color pattern and silhouette are completely new in the upright Asiatic divisions of lilies suited to forcing and to mass commercial cultivation. The plant is highly resistant to disease and shows high tolerance of virus, it is an excellent garden plant, and the bulbs may be precooled and forced throughout the year for pot plant production, the clone being vigorous and a good grower and propagator.

1 Drawing Sheet

BACKGROUND OF THE INVENTION

This new variety of lily plant originated as a seedling selected from a group of seedlings planted by me at Sandy, Oreg., with seeds resulting from my crossing of a very short, cream-flowered clonal selection from the 'Pastel Hybrids' strain with pollen from a red-orange flowered seedling from 'Connecticut Lemonglow' by 'Red Carpet', with the object of producing lilies in shades of orange and red well suited to forcing for pot plant production out-of-season. This particular seedling was selected for propagation and test because of the large size of its flowers having broad tepals, a vivid red coloration, and extremely inconspicuous spotting, this color pattern being unique in this type of lily. Asexual propagation of this seedling was done by me and under my direction at Sandy, Oreg., and carried on through several successive generations by bulb scale propagation and by natural propagation of bulblets, which demonstrated that the novel and distinctive characteristics of the selected seedling are fixed and hold true under asexual propagation from generation to generation.

Work with this new plant shows that the variety remains short and is not overly susceptible to bud abortion when forced into flower out-of-season as a pot plant. In addition, the clone possesses to a high degree the desirable characteristics of hybrid vigor, great hardiness, and disease resistance, as well as having all of the desired characteristics of excellence of form, color and habit.

The plant has shown that it is well suited to forcing out-of-season when the bulbs are dug at the appropriate time and properly precooled. For example, October-dug bulbs, properly precooled and potted in January, will flower under glass in western Oregon in an average of sixty-five to eighty days with no supplementary lighting and at moderate greenhouse temperatures.

DESCRIPTION OF THE DRAWING

This new variety of lily plant is illustrated in the accompanying full color photographic drawing which shows a fully opened bloom and illustrates the flower form and the tepal arrangement, as well as the novel and distinctive red, inconspicuously spotted flower tepals, the colors shown being as nearly true to that herein specified as is reasonably possible to obtain by professional photographic procedures.

DESCRIPTION OF THE NEW VARIETY

The following is a detailed description of my new variety of Asiatic hybrid lily with nomenclature according to The International Lily Register, Second Edition, 1969, by The Royal Horticultural Society of London, England, the color designations herein specified being according to The R.H.S. Colour Chart published by the society in 1966.

THE PLANT

Origin: Seedling.

Parentage:

*Seed parent.*—A short, cream-flowered clonal selection from a collection of Lilium 'Pastel Hybrids' plants.

*Pollen parent.*—A red-orange flowered selection from seedlings of 'Connecticut Lemonglow' (unpatented) by 'Red Carpet' (unpatented).

Classification:

*Horticultural.*—Division IA, Upright Asiatic Hybrid Lily from The Horticultural Classification of Lilies by The Royal Horticultural Society of London.

*Commercial.*—Hybrid Lilium Clone.

Form: Single stem, erect and stately.

Height: About 35 to 45 cm. for stems produced by glasshouse forcing of bulbs of about 12 to 18 cm. in circumference; provided that their light levels are adequate. Low light levels may cause "stretching".

Growth: Vigorous and upright.

Foliage:

*Quantity.*—Abundant.

*Leaf size.*—About 8 to 12 cm. long and 1 cm. wide.

*Leaf shape.*—Lanceolate with acuminate tip.

*Texture.*—Leathery.

*Aspect.*—Glossy.

*Color.*—Medium green, lighter on the under side.

The bulb:

*Size.*—Various, ranging to 25 cm. in circumference as commercially used.

*Color.*—White.

THE BUD

Form: Long ovoid with obtuse tip.

Size: About 8 to 9 cm. long and about 7 cm. in circumference just prior to opening.

Opening rate: The bud opens slowly, in about one hour in response to morning light.

Color: Red, 43B-C, at the center portion of the bud and slightly lighter at the apex and base of the bud just prior to opening and as the tepals unfurl.

Peduncle:

*Length.*—About 4 to 6 cm., in average. The peduncle may elongate if the light levels are too low or if the bulbs have been improperly stored prior to forcing.

*Color.*—Medium green.

THE FLOWER

Blooming habit: Once annually and profusely in midseason.

Size:

*Average diameter.*—About 12 to 17 cm.

Borne: As a single, compact raceme inflorescence producing about nine to twelve buds from a bulb of about 12 to 16 cm. in circumference.

Shape: Cup-shaped upon first opening and flattening somewhat as the tepals recurve by the second day.

Tepalage: Typical of genus Lilium with six tepals in hexagonal arrangement, the inner tepals alternating with the outer tepals.

*Size.*—The outer tepals average about 2.5 to 3.0 cm. wide. The inner tepals average about 3.5 to 4.0 cm. wide.

*Shape.*—Elliptical with attenuate base.

*Color.*—Vivid red, with a base color of Red, 46A-B, to Red, 44A. This color is produced by a magenta pigment in the upper epidermal cell layers of the tepals, overlaying the Red-Orange, 34A-B, pigmentation of the mesophyll layers. This causes the red color to vary somewhat under different light levels and to appear to be "brushed on" more heavily in some areas. The tepal margins show the Red-Orange mesophyll color, 34A-B, in a band about 1 to 2 mm. wide. The nectaries are overlaid with white pubescence.

*Spotting.*—Each inner tepal has about ten to fifteen tiny, inconspicuous magenta spots at its base. The outer tepals are unspotted.

Aspect: Shiny.

Color changes: The flower may become slightly less red and more orange as it ages, depending upon light levels; there is usually only a slight color change if the light levels are adequate for cut flower and pot plant maintenace.

Longevity: The tepals stay on the stems for about three weeks.

Pedicel:

*Length.*—About 4 to 8 cm., in average.

*Character.*—Sturdy and ascending up to about 60° from the horizontal.

*Color.*—Medium to dark green.

Fragrance: None.

Lasting quality: The flower is long lasting, substantially three weeks.

Disease resistance: The flower and plant are resistant to disease; in particular, they are resistant to Fusarium Bulb Rot and Botrytis Blight.

THE REPRODUCTIVE ORGANS

Stamens:

*Number.*—Six, with arrangement typical of genus Lilium.

*Pollen and anthers (dehisced).*—Color: Greyed Orange, 169A to 171A.

*Filaments.*—Length: About 5 cm. Color: Soft Red-Orange, 33B.

Pistil:

*Number.*—One.

*Style.*—Length: About 5 cm.

*Stigma.*—Small, about 1 to 2.5 mm. wide. Color: Soft Plum, 59C.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most closely resembles 'Red Carpet' (unpatented) but has a richer, more red and less "brown" color, broader and thicker tepals, a lighter pollen color, a more compact inflorescence with shorter pedicels, and a higher bud count. The plant is shorter in height and with shorter leaves than 'Red Carpet' and it is also more reliable and uniform in its forcing performance with the capability of being forced into flower much more rapidly than 'Red Carpet'.

I claim:

1. The new and distinctive variety of Asiatic hybrid lily plant and parts thereof, substantially as herein shown and described, characterized in particular by its rich red, broad tepalled and inconspicously spotted flowers; and by its short-stemmed, longer and abundantly leaved, upright flowering silhouette, ideal for pot plant culture.

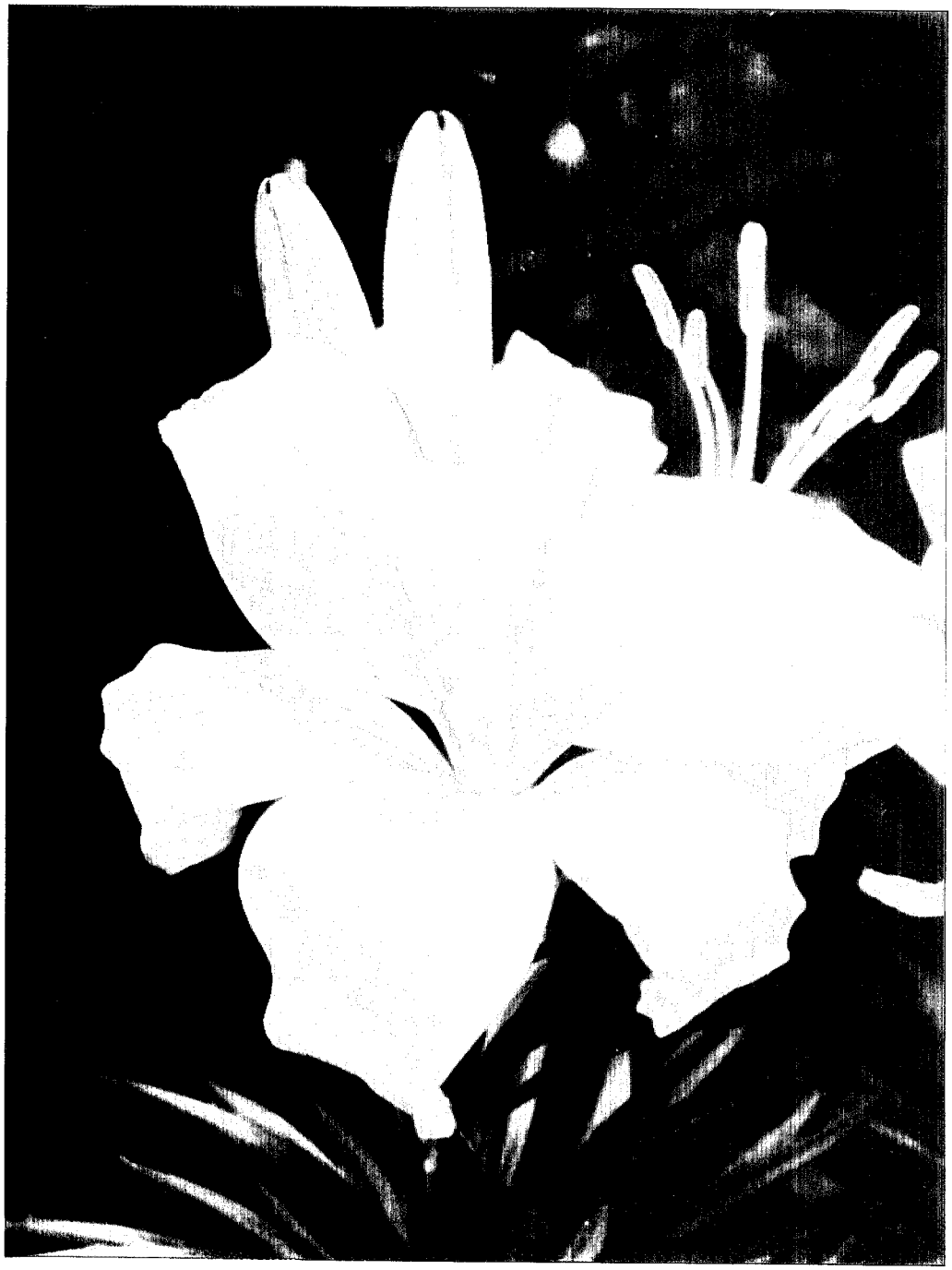

* * * * *